US008822965B2

(12) United States Patent
Asaba (10) Patent No.: US 8,822,965 B2
(45) Date of Patent: Sep. 2, 2014

(54) CHARGED PARTICLE BEAM IRRADIATION APPARATUS

(71) Applicant: Sumitomo Heavy Industries, Ltd., Tokyo (JP)

(72) Inventor: Toru Asaba, Ehime (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 13/939,914

(22) Filed: Jul. 11, 2013

(65) Prior Publication Data

US 2014/0014851 A1  Jan. 16, 2014

(30) Foreign Application Priority Data

Jul. 12, 2012  (JP) ................ 2012-156669

(51) Int. Cl.
*H01J 3/08* (2006.01)
*H05H 7/12* (2006.01)
*H05H 7/00* (2006.01)

(52) U.S. Cl.
CPC ............ *H01J 3/08* (2013.01); *H05H 2007/007* (2013.01); *H05H 7/00* (2013.01); *H05H 2007/004* (2013.01); *H05H 7/12* (2013.01)
USPC .................. 250/515.1; 250/492.3; 250/505.1; 250/396 R; 250/492.1

(58) Field of Classification Search
USPC ......... 250/492.3, 505.1, 396 R, 492.1, 515.1; 378/147, 145, 159, 150
See application file for complete search history.

(56) References Cited

U.S. PATENT DOCUMENTS

| 3,322,950 | A  | * | 5/1967  | Bailey et al. ................. 378/65 |
| 4,794,259 | A  | * | 12/1988 | Sanderson et al. ............ 250/397 |
| 4,853,640 | A  | * | 8/1989  | Matsumoto et al. ........... 315/503 |
| 5,969,367 | A  | * | 10/1999 | Hiramoto et al. .......... 250/492.3 |
| 5,986,274 | A  | * | 11/1999 | Akiyama et al. ........... 250/492.3 |
| 6,127,688 | A  | * | 10/2000 | Wu ............................ 250/505.1 |
| 6,433,349 | B2 | * | 8/2002  | Akiyama et al. ........... 250/505.1 |
| 6,777,700 | B2 | * | 8/2004  | Yanagisawa et al. ....... 250/492.3 |
| 7,053,389 | B2 | * | 5/2006  | Yanagisawa et al. ....... 250/492.3 |
| 7,297,967 | B2 | * | 11/2007 | Yanagisawa et al. ....... 250/492.3 |
| 7,394,082 | B2 | * | 7/2008  | Fujimaki et al. ........... 250/492.3 |
| 7,400,434 | B2 | * | 7/2008  | Brahme et al. ............... 359/237 |
| 7,449,701 | B2 | * | 11/2008 | Fujimaki et al. ........... 250/492.3 |
| 7,589,334 | B2 | * | 9/2009  | Hiramoto et al. ......... 250/492.21 |
| 8,218,728 | B2 | * | 7/2012  | Karch ........................ 378/98.11 |
| 8,263,954 | B2 | * | 9/2012  | Iwata ......................... 250/505.1 |
| 8,330,132 | B2 | * | 12/2012 | Guertin et al. .............. 250/515.1 |
| 8,536,548 | B2 | * | 9/2013  | Otani et al. ................ 250/492.3 |
| 8,575,564 | B2 | * | 11/2013 | Iwata ......................... 250/396 R |
| 8,586,948 | B2 | * | 11/2013 | Pu et al. ..................... 250/492.1 |

(Continued)

FOREIGN PATENT DOCUMENTS

JP      2009-236867 A      10/2009

*Primary Examiner* — David A Vanore
(74) *Attorney, Agent, or Firm* — Rader, Fishman & Grauer PLLC (57) ABSTRACT

A charged particle beam irradiation apparatus includes: a scanning electromagnet that scans a charged particle beam; and a degrader that is provided on a downstream side of the scanning electromagnet in a scanning direction of the charged particle beam and adjusts a range of the charged particle beam by reducing energy of the charged particle beam. The degrader is configured to be closer to an upstream side in the scanning direction of the charged particle beam, outward in the scanning direction.

10 Claims, 9 Drawing Sheets

(56) References Cited

U.S. PATENT DOCUMENTS

| | | | |
|---|---|---|---|
| 2003/0198319 A1* | 10/2003 | Toth et al. | 378/159 |
| 2006/0226372 A1* | 10/2006 | Yanagisawa et al. | 250/396 R |
| 2006/0256914 A1* | 11/2006 | Might et al. | 378/57 |
| 2007/0040127 A1* | 2/2007 | Brahme et al. | 250/389 |
| 2007/0228304 A1* | 10/2007 | Nishiuchi et al. | 250/505.1 |
| 2012/0119105 A1* | 5/2012 | Iwata | 250/396 ML |
| 2012/0215049 A1* | 8/2012 | Otani et al. | 600/1 |
| 2013/0056646 A1* | 3/2013 | Iwata | 250/396 R |
| 2013/0231516 A1* | 9/2013 | Loo et al. | 600/1 |
| 2013/0274536 A1* | 10/2013 | Iwata | 600/1 |
| 2013/0299721 A1* | 11/2013 | Sasai | 250/492.3 |
| 2014/0014851 A1* | 1/2014 | Asaba | 250/396 R |
| 2014/0018603 A1* | 1/2014 | Asaba | 600/1 |

* cited by examiner

|  | SAD [mm] | DEGRADER THICKNESS (MAXIMUM) [mm] | MAXIMUM RADIATION FIELD (SINGLE SIDE) [mm] | PASSAGE DISTANCE DIFFERENCE (MAXIMUM) WATER-EQUIVALENT LENGTH [mm] |
|---|---|---|---|---|
| EXAMPLE 1 | 2180 | 128 | 100 | 0.156134 |
| EXAMPLE 2 | 1500 | 128 | 200 | 1.314008 |

CHARGED PARTICLE BEAM IRRADIATION APPARATUS

INCORPORATION BY REFERENCE

Priority is claimed to Japanese Patent Application No. 2012-156669, filed Jul. 12, 2012, the entire content of each of which is incorporated herein by reference.

BACKGROUND

1. Technical Field

The present invention relates to a charged particle beam irradiation apparatus for irradiating a charged particle beam.

2. Description of the Related Art

A charged particle beam irradiation apparatus for irradiating a charged particle beam is disclosed in the related art. The charged particle beam irradiation apparatus disclosed in the related art is an apparatus for performing treatment by irradiating a tumor within the body of a patient with a charged particle beam. The charged particle beam irradiation apparatus includes a cyclotron that generates a charged particle beam by accelerating a charged particle, a scanning electromagnet that scans the charged particle beam, and a degrader that is provided on a downstream side of the scanning electromagnet in the scanning direction of the charged particle beam and adjusts the range of the charged particle beam by reducing the energy of the charged particle beam. The degrader is a plate-like member that extends with a fixed thickness in a scanning direction perpendicular to the irradiation direction of the charged particle beam.

Figure 5:
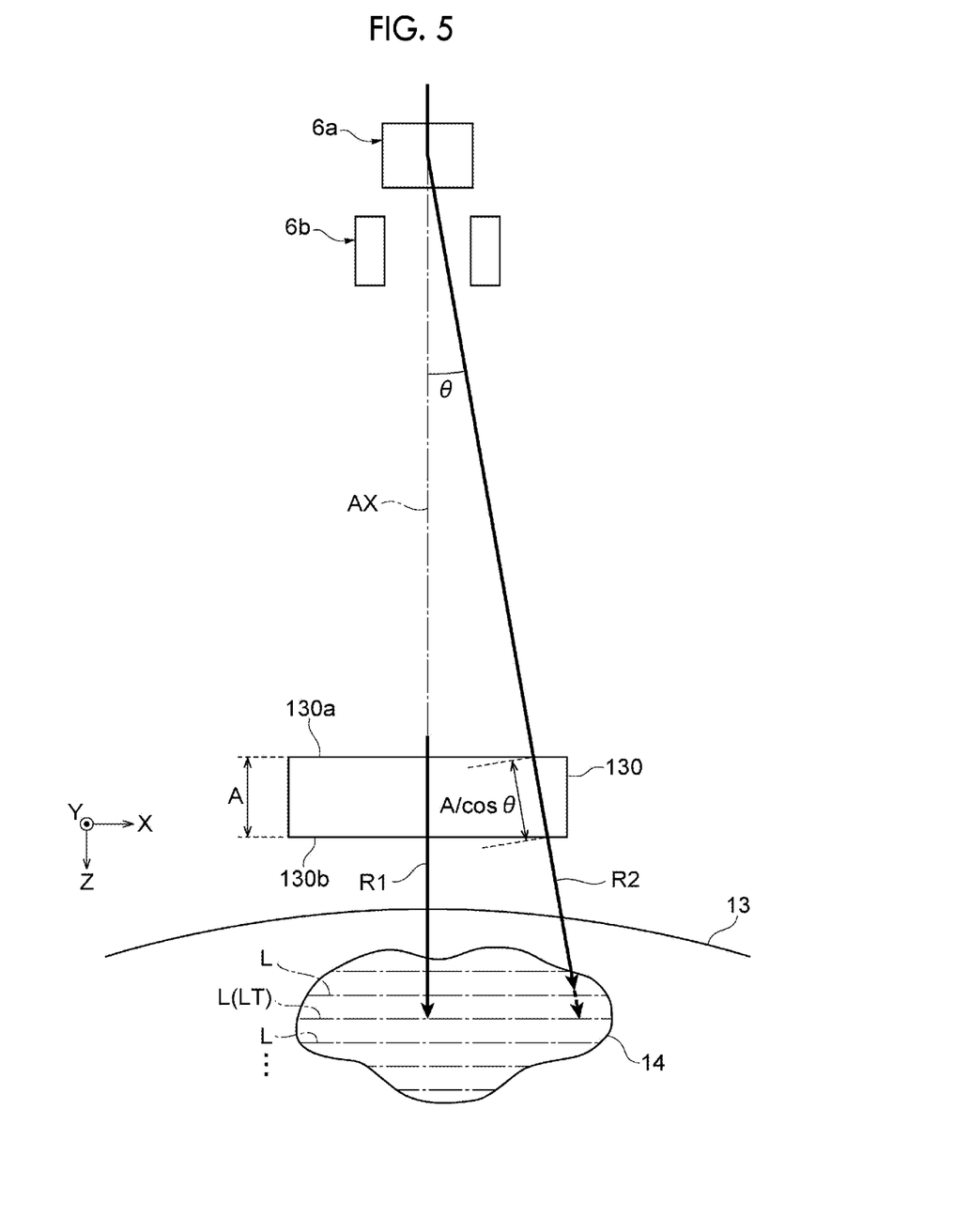
FIG. 5 shows the configuration of a degrader in the related art, and is a schematic diagram showing the relationship between the deflection angle of a charged particle beam and the passing distance within the degrader.

The degrader of the charged particle beam irradiation apparatus in the related art has a rectangular cross-section in the irradiation direction of the charged particle beam (for example, refer to FIG. 5). When such a degrader is used, a charged particle beam made to go straight without being deflected by the scanning electromagnet is perpendicularly incident on the degrader. Accordingly, the passing distance of the charged particle beam within the degrader is equal to the thickness of the degrader (thickness of the degrader in the Z direction in FIG. 5). On the other hand, in the case of a charged particle beam deflected by the scanning electromagnet, the passing distance of the charged particle beam within the degrader is increased if the deflection angle is large. In this case, since the energy of the charged particle beam decreases as the passing distance of the charged particle beam within the degrader increases, the range of the charged particle beam becomes short.

SUMMARY

According to an embodiment of the present invention, there is provided a charged particle beam irradiation apparatus including: a scanning electromagnet that scans a charged particle beam; and a degrader that is provided on a downstream side of the scanning electromagnet in a scanning direction of the charged particle beam and adjusts a range of the charged particle beam by reducing energy of the charged particle beam. The degrader is configured to be closer to an upstream side in the scanning direction of the charged particle beam, outward in the scanning direction.

DETAILED DESCRIPTION

Since the range of the charged particle beam changes with the deflection angle, an actual dose of the charged particle beam irradiated to a predetermined position of the tumor is different from that planned in the treatment planning. Accordingly, there is a problem in that the irradiation accuracy of the charged particle beam is reduced.

It is desirable to provide a charged particle beam irradiation apparatus capable of irradiating a charged particle beam accurately.

A charged particle beam having a small deflection angle by the scanning electromagnet passes through a portion of the degrader located at the inside in the scanning direction, and a charged particle beam having a large deflection angle by the scanning electromagnet passes through a portion of the degrader located at the outside in the scanning direction. For such a charged particle beam, the degrader is configured to be closer to the upstream side in the scanning direction of the charged particle beam, outward in the scanning direction. Thus, the overall shape of the degrader in the scanning direction becomes a shape curved with respect to the scanning electromagnet that is the origin of deflection of the charged particle beam. Therefore, it is possible to suppress an increase in the passing distance of the charged particle beam, which has a large deflection angle, within the degrader. As a result, since it is possible to reduce a difference between the passing distance of the charged particle beam having a small deflection angle within the degrader and the passing distance of the charged particle beam having a large deflection angle within the degrader, it is possible to suppress a change in the range of the charged particle beam due to the deflection angle. In this manner, it is possible to irradiate a charged particle beam with high accuracy.

In addition, in the charged particle beam irradiation apparatus, it is preferable that the degrader have an upstream side surface located on the upstream side in the scanning direction of the charged particle beam and a downstream side surface located on a downstream side in the scanning direction of the charged particle beam, the upstream side surface be configured to be closer to the upstream side in the scanning direction of the charged particle beam, outward in the scanning direction, and the downstream side surface be configured to be closer to the upstream side in the scanning direction of the charged particle beam, outward in the scanning direction. With this configuration, the overall shape of the degrader in the scanning direction can be made to be a curved shape in a state where the thickness of the degrader is constant or approximately constant. Accordingly, the passing distance of the charged particle beam within the degrader according to the deflection angle can be made to be constant or approximately constant.

In addition, in the charged particle beam irradiation apparatus, it is preferable that the degrader have a plurality of stepped portions that are located on the upstream side in the scanning direction of the charged particle beam stepwise, outward in the scanning direction. The shape of the degrader can be made to be an approximately curved shape in the scanning direction by forming the plurality of stepped portions. As a result, it is possible to easily perform the machining of the degrader for forming a shape in which the change in the range of the charged particle beam according to the deflection angle can be suppressed.

In addition, in the charged particle beam irradiation apparatus, it is preferable that the degrader be curved so as to be closer to the upstream side in the scanning direction of the charged particle beam, outward in the scanning direction. Since the degrader is curved, the passing distance of the charged particle beam within the degrader according to the deflection angle can be made to be exactly constant or approximately constant in the entire region in the scanning direction. As a result, it is possible to further improve the accuracy of irradiation of the charged particle beam.

In addition, in the charged particle beam irradiation apparatus, it is preferable that the scanning direction include a first scanning direction and a second scanning direction perpendicular to the first scanning direction and that the degrader be configured to be closer to the upstream side in the first scanning direction of the charged particle beam, outward in the first scanning direction and closer to the upstream side in the second scanning direction of the charged particle beam, outward in the second scanning direction. Accordingly, at any position in both the first and second scanning directions, the passing distance of the charged particle beam within the degrader according to the deflection angle can be made to be constant or approximately constant. As a result, it is possible to further improve the accuracy of irradiation of the charged particle beam.

Hereinafter, preferred embodiments of the present invention will be described in detail with reference to the accompanying drawings. In addition, in the following explanation, the same or corresponding components are denoted by the same reference numerals and repeated explanation thereof will be omitted.

Figure 1:
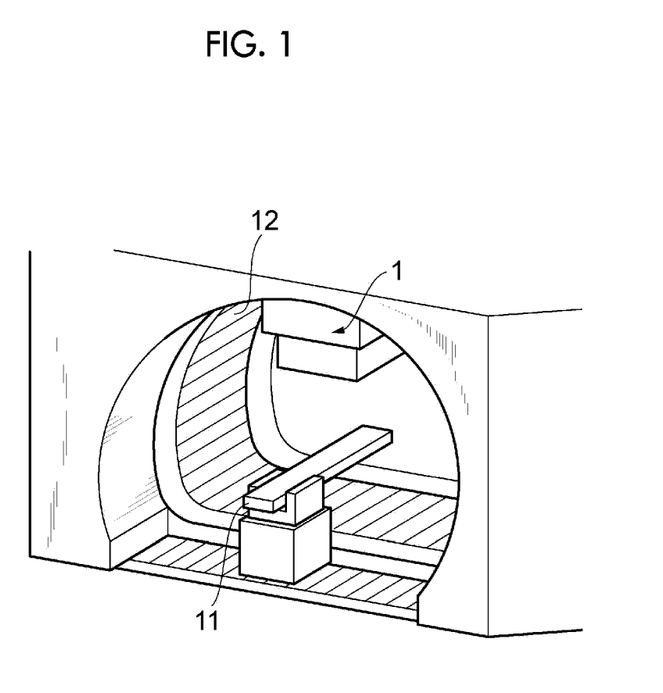
FIG. 1 is a perspective view of a charged particle beam irradiation apparatus according to an embodiment of the present invention.

FIG. 1 is a perspective view of a charged particle beam irradiation apparatus according to an embodiment of the present invention. As shown in FIG. 1, a charged particle beam irradiation apparatus 1 is fixed to a rotating gantry 12 that is provided so as to surround a treatment table 11. The charged particle beam irradiation apparatus 1 is rotatable around the treatment table 11 by the rotating gantry 12. In addition, the charged particle beam irradiation apparatus 1 is a charged particle beam treatment apparatus for treating a tumor.

Figure 2:
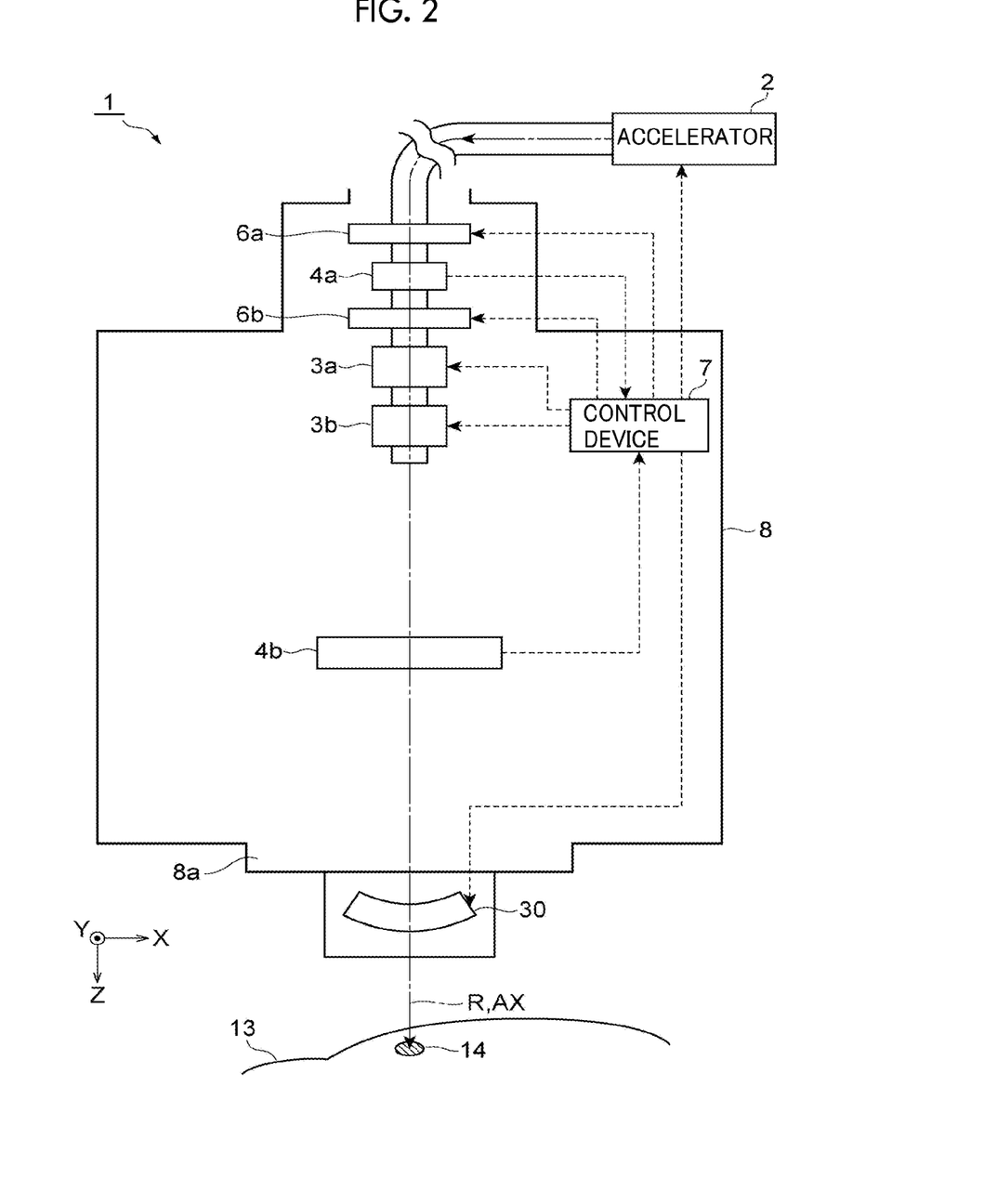
FIG. 2 is a schematic diagram showing the configuration of a charged particle beam irradiation apparatus that irradiates a charged particle beam using a scanning method.
Figure 3:
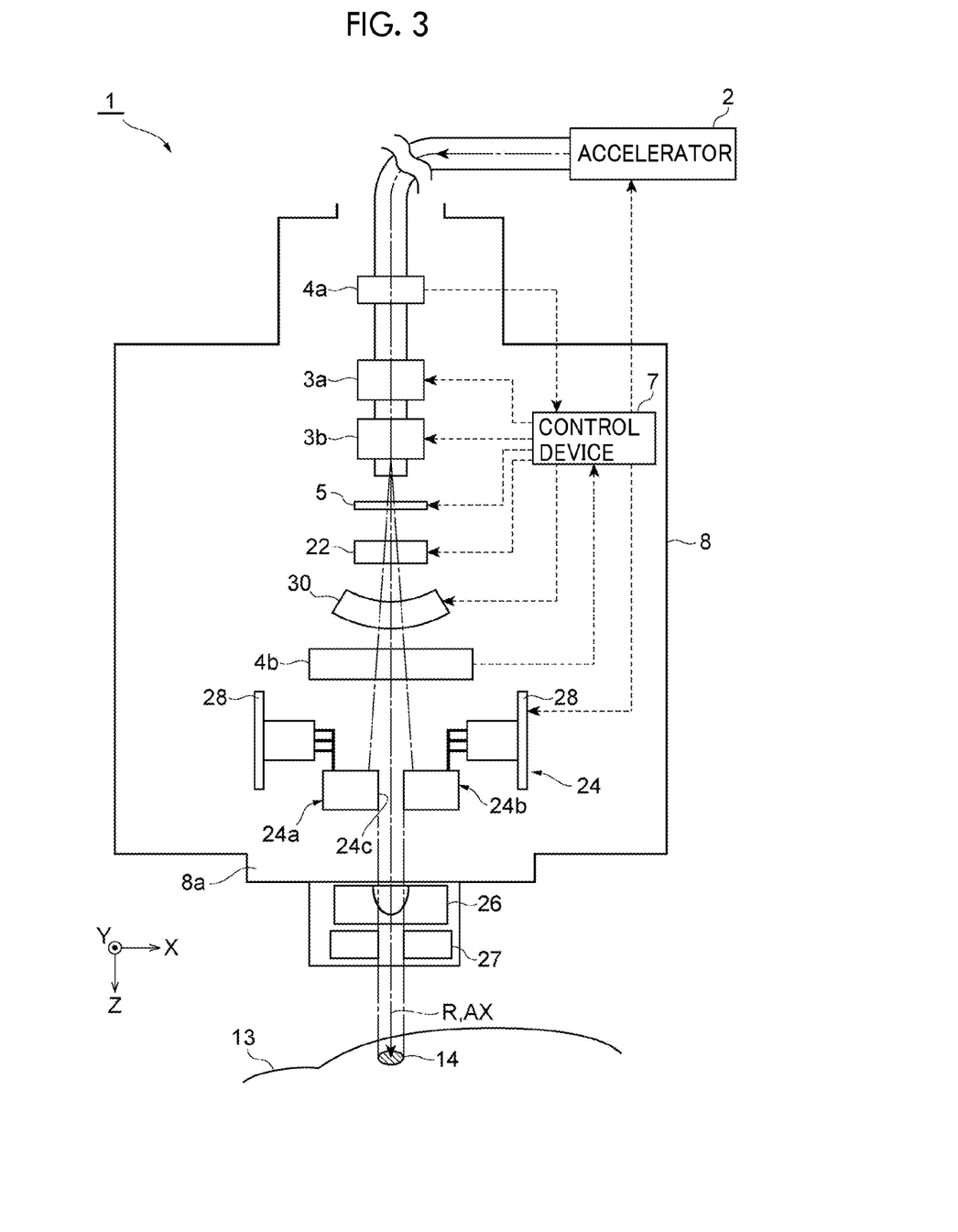
FIG. 3 is a schematic diagram showing the configuration of a charged particle beam irradiation apparatus that irradiates a charged particle beam using a wobbler method.

FIG. 2 is a schematic diagram showing the configuration of a charged particle beam irradiation apparatus that irradiates a charged particle beam using a scanning method. FIG. 3 is a schematic diagram showing the configuration of a charged particle beam irradiation apparatus that irradiates a charged particle beam using a wobbler method. As shown in FIGS. 2 and 3, the charged particle beam irradiation apparatus 1 irradiates a tumor (irradiation object) 14 within the body of a patient 13 with a charged particle beam R. The charged particle beam R is obtained by accelerating a charged particle at high speed. For example, a proton beam, a heavy particle (heavy ion) beam, and the like can be mentioned. In addition, the wobbler method is also referred to as a broad beam method.

In addition, the following explanation will be given using terms of "X direction", "Y direction", and "Z direction". The "Z direction" is a direction in which the base axis AX of the charged particle beam R extends. In addition, the "base axis AX" is assumed to be an irradiation axis of the charged particle beam R when the charged particle beam R is not deflected by scanning electromagnets 3a and 3b to be described later. FIGS. 2 and 3 show that the charged particle beam R is irradiated along the base axis AX. In addition, in the following explanation, a direction in which the charged particle beam R is irradiated along the base axis AX is assumed to be the "irradiation direction of charged particle beam R". The "X direction" is one direction within the plane perpendicular to the Z direction. The "Y direction" is a direction perpendicular to the X direction within the plane perpendicular to the Z direction.

First, the configuration of the charged particle beam irradiation apparatus 1 according to the scanning method will be described with reference to FIG. 2. As shown in FIG. 2, the charged particle beam irradiation apparatus 1 includes an accelerator 2, scanning electromagnets 3a and 3b, monitors 4a and 4b, convergence bodies 6a and 6b, a degrader 30, and a control device 7. The scanning electromagnets 3a and 3b, the monitors 4a and 4b, the convergence bodies 6a and 6b, the degrader 30, and the control device 7 are housed in an irradiation nozzle 8. However, the control device 7 may be provided outside the irradiation nozzle 8.

The accelerator 2 is a source that generates the charged particle beam R continuously by accelerating charged particles. As examples of the accelerator 2, a cyclotron, a synchrotron, a cyclo-synchrotron, and a linac can be mentioned. The charged particle beam R generated in the accelerator 2 is transferred to the irradiation nozzle 8 by the beam transfer system. The accelerator 2 is connected to the control device 7, and the current or the like of the charged particle beam R supplied from the accelerator 2 is controlled by the control device 7.

The scanning electromagnets 3a and 3b are formed by a pair of electromagnets. By changing the magnetic field between a pair of electromagnets according to the signal supplied from the control device 7, the charged particle beam R passing between the electromagnets is scanned. The X-direction scanning electromagnet 3a scans the charged particle beam R in the X direction (first scanning direction), and the Y-direction scanning electromagnet 3b scans the charged particle beam R in the Y direction (second scanning direction perpendicular to the first scanning direction). These scanning electromagnets 3a and 3b are disposed in this order on the downstream side of the accelerator 2 on the base axis AX. In addition, the scanning electromagnets 3a and 3b may also be disposed in order of the scanning electromagnets 3b and 3a without being limited to the arrangement based on the above order.

The monitor 4a monitors (detects) the beam position of the charged particle beam R, and the monitor 4b monitors (detects) the absolute value of the dose of the charged particle beam R and the dose distribution of the charged particle beam R. Each of the monitors 4a and 4b outputs the monitoring information (detection value) to the control device 7. The monitor 4a is disposed on the downstream side of the accelerator 2 and on the upstream side of the X-direction scanning electromagnet 3a on the base axis AX of the charged particle beam R. The monitor 4b is disposed on the downstream side of the Y-direction scanning electromagnet 3b on the base axis AX.

The convergence bodies 6a and 6b narrow the charged particle beam R so as to converge, for example. Electromagnets are used as convergence bodies 6a and 6b herein. The convergence body 6a is disposed between the accelerator 2 and the monitor 4a on the base axis AX, and the convergence body 6b is disposed between the monitor 4a and the scanning electromagnet 3a on the base axis AX.

The degrader 30 adjusts the range of the charged particle beam R by reducing the energy of the charged particle beam R passing therethrough. In addition, when adjusting the range, rough adjustment is performed by a degrader (not shown) that is provided immediately after the accelerator 2, and fine adjustment is performed by the degrader 30 in the irradiation nozzle 8. The degrader 30 is located on the base axis AX, is provided on a downstream side of the scanning electromagnets 3a and 3b in the scanning direction of the charged particle beam R and adjusts the maximum arrival depth of the charged particle beam R within the body of the patient 13. The degrader 30 is a plate-like member extending in the X and Y directions. In addition, in the present embodiment, the "range" is a movement distance of the charged particle beam R until the charged particle beam R loses kinetic energy and stops. More specifically, assuming that the maximum dose is 100%, the range is a depth, at which the dose is 90%, on a deeper side than the irradiation distance (depth) when the maximum dose is obtained. When irradiating the tumor 14 with the charged particle beam R, the tumor 14 is virtually divided into a plurality of layers L in a Z direction (for example, refer to FIG. 5), and irradiation is performed in an irradiation range set in each layer L while scanning the charged particle beam R along a predetermined scanning pattern. After the irradiation of the charged particle beam R with respect to one layer L is completed, the degrader 30 (in addition, a degrader provided immediately after the accelerator 2 may also used) adjusts the range, and irradiation of the charged particle beam R with respect to another layer L is performed. The degrader 30 is disposed at a position of about 1500 mm to 2000 mm from the Y-direction scanning electromagnet 3b.

The range of the charged particle beam R is adjusted by changing the passing distance of the charged particle beam R within the degrader 30. For example, it is possible to adjust the range by replacing the degrader 30 itself disposed on the irradiation axis of the charged particle beam R with a degrader having a different thickness. Alternatively, it is also possible to adjust the range by changing the number of degraders 30 disposed on the base axis AX of the charged particle beam R in a configuration where a plurality of degraders 30 can be disposed in the Z direction. In this case, the arrangement and removal of the degrader 30 onto and from the base axis AX of the charged particle beam R are possible by providing an actuator, which can reciprocate in the plane perpendicular to the Z direction, for each degrader 30 and controlling the actuator. In addition, although the detailed configuration will be described later, the degrader 30 has a curved shape in the present embodiment. Accordingly, when using a reciprocable actuator, it is preferable to separate the upstream side surface of one degrader 30 from the downstream side surface of another degrader 30 adjacent on the upstream side so that the degraders 30 do not interfere with each other.

A position where the degrader 30 is provided is not particularly limited as long as it is a more downstream side than the scanning electromagnets 3a and 3b. However, when the scanning method is adopted, it is preferable to provide the degrader 30 on the more downstream side than the monitor 4b. In the present embodiment, the degrader 30 is provided at a distal end 8a of the irradiation nozzle 8. In addition, the distal end of the irradiation nozzle 8 is an end on the downstream side in the scanning direction of the charged particle beam R.

The control device 7 is configured to include a CPU, a ROM, and a RAM, for example. The control device 7 controls the accelerator 2, the scanning electromagnets 3a and 3b, and the convergence bodies 6a and 6b on the basis of the monitoring information output from the monitors 4a and 4b.

When irradiating the charged particle beam R in the scanning method using the charged particle beam irradiation apparatus 1 shown in FIG. 2, the degrader 30 that can perform adjustment to the predetermined range is set, and the convergence bodies 6a and 6b are changed to the operating state (ON) so that the charged particle beam R passing therethrough converges.

Then, the charged particle beam R is emitted from the accelerator 2. The emitted charged particle beam R is scanned by controlling the scanning electromagnets 3a and 3b, and the range of the charged particle beam R is adjusted by the degrader 30. In this manner, the charged particle beam R is irradiated while being scanned within the irradiation range in one layer L set in the Z direction for the tumor 14. After the irradiation to one layer L is completed, the charged particle beam R is irradiated to the next layer L.

The configuration of a charged particle beam irradiation apparatus according to the wobbler method will be described with respect to FIG. 3. As shown in FIG. 3, the charged particle beam irradiation apparatus 1 includes the accelerator 2, the scanning electromagnets 3a and 3b, the monitors 4a and 4b, a scatterer 5, a ridge filter 22, a multi-leaf collimator 24, a bolus 26, a patient collimator 27, the degrader 30, and the control device 7. The scanning electromagnets 3a and 3b, the monitors 4a and 4b, the scatterer 5, the ridge filter 22, the multi-leaf collimator 24, the bolus 26, the patient collimator 27, degrader 30, and the control device 7 are housed in the irradiation nozzle 8. However, the control device 7 may be provided outside the irradiation nozzle 8. In addition, the same portions as in the charged particle beam irradiation apparatus 1 shown in FIG. 2 will be omitted.

The scatterer 5 diffuses the charged particle beam R passing therethrough into a wide beam having a spread in a direction perpendicular to the irradiation axis. The scatterer 5 has a plate shape, and is formed of tungsten having a thickness of several millimeters, for example. The scatterer 5 is disposed on the downstream side of the scanning electromagnet 3b and the upstream side of the monitor 4b on the base axis AX.

The ridge filter 22 adjusts the dose distribution of the charged particle beam R. Specifically, the ridge filter 22 gives a spread-out Bragg peak (SOBP) to the charged particle beam R so as to correspond to the thickness (length in the irradiation direction) of the tumor 14 within the body of the patient 13. The ridge filter 22 is disposed on the downstream side of the scatterer 5 and the upstream side of the monitor 4b on the base axis AX.

The degrader 30 is disposed between the ridge filter 22 and the monitor 4b on the base axis AX. The degrader 30 has the same function and configuration as those described in FIG. 2, and can adjust the range using the same method. The degrader 30 is disposed at a position of about 1000 mm to 1800 mm from the scatterer 5.

The multi-leaf collimator (hereinafter, referred to as an "MLC") 24 serves to shape the shape (planar shape) of the charged particle beam R in a plane direction perpendicular to the irradiation direction, and has light shielding portions 24a and 24b including a plurality of comb teeth. The light shielding portions 24a and 24b are disposed so as to face each other, and an opening 24c is formed between the light shielding portion 24a and 24b. The MLC 24 cuts out the charged particle beam R having a contour corresponding to the shape of the opening 24c by allowing the charged particle beam R to pass through the opening 24c.

In addition, the MLC 24 can change the position and shape of the opening 24c by moving the light shielding portion 24a and 24b back and forth in a direction perpendicular to the Z direction. In addition, the MLC 24 is guided along the irradiation direction by a linear guide 28, and is movable along the Z direction. The MLC 24 is disposed on the downstream side of the monitor 4b.

The bolus 26 shapes the three-dimensional shape of a portion of the maximum arrival depth of the charged particle beam R according to the shape of a maximum depth portion of the tumor 14. The shape of the bolus 26 is calculated on the basis of the outline of the tumor 14 and the electron density of surrounding tissue calculated from the data of X-ray CT, for example. The bolus 26 is disposed on the downstream side of the MLC 24 on the base axis AX. The patient collimator 27 finally shapes the planar shape of the charged particle beam R according to the planar shape of the tumor 14. The patient collimator 27 is disposed on the downstream side of the bolus 26 on the base axis AX. The patient collimator 27 may be used instead of the MLC 24, or both the MLC 24 and the patient collimator 27 may be used. The bolus 26 and the patient collimator 27 are provided at the distal end 8a of the irradiation nozzle 8.

When irradiating the charged particle beam R in the wobbler method using the charged particle beam irradiation apparatus 1 shown in FIG. 3, the degrader 30 that can perform adjustment to the predetermined range is set, and the light shielding portion 24a and 24b of the MLC 24 are moved back and forth so that the opening 24c has a predetermined shape. Then, the charged particle beam R is emitted from the accelerator 2. The emitted charged particle beam R is scanned so as to draw a circle by the scanning electromagnets 3a and 3b and is diffused by the scatterer 5, and is then shaped and adjusted by the ridge filter 22, the degrader 30, the MLC 24, the bolus 26, and the patient collimator 27. As a result, the charged particle beam R is irradiated to the tumor 14 so as to have a uniform irradiation range along the shape of the tumor 14.

In addition, it is also possible to adopt a configuration to perform both the scanning method and the wobbler method using the same charged particle beam irradiation apparatus 1. That is, it is possible to provide the components shown in FIG. 2 and the components shown in FIG. 3, and remove the components used only in the wobbler method when the scanning method is adopted and remove the components used only in the scanning method when the wobbler method is adopted.

Next, details of the configuration of the degrader 30 will be described with reference to FIGS. 4A and 4B.

Figure 4A:
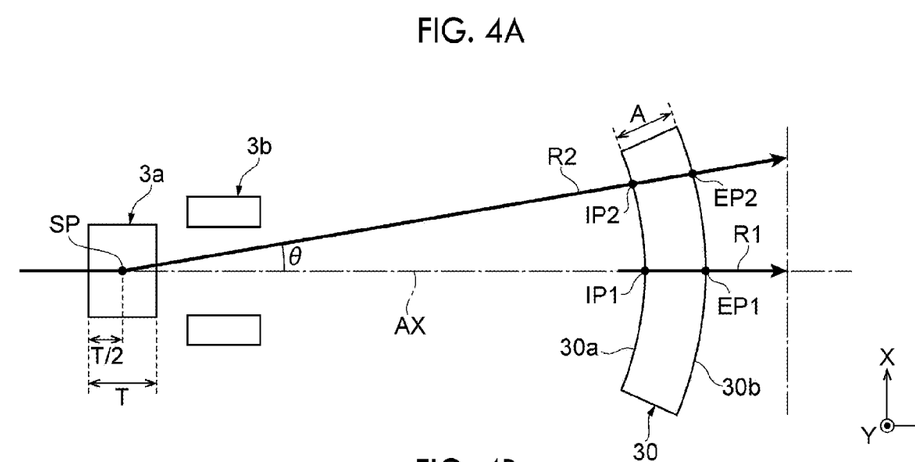
FIGS. 4A and 4B are schematic diagrams showing the configuration of a degrader of the charged particle beam irradiation apparatus according to the embodiment of the present invention.
Figure 4B:
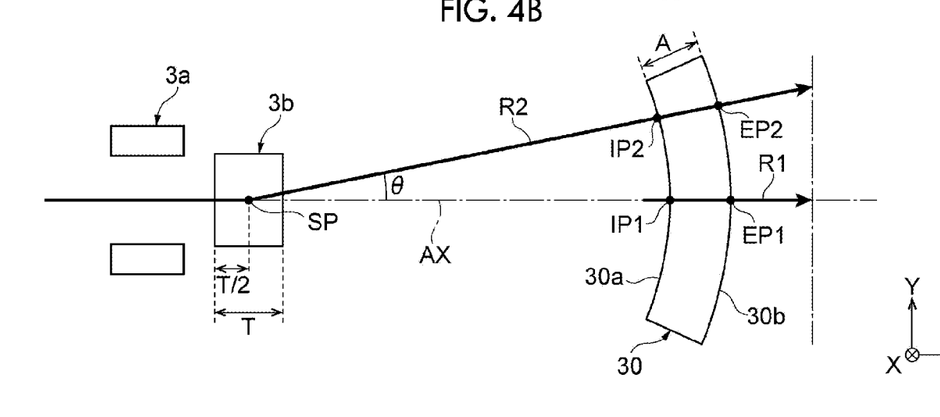

As shown in FIGS. 4A and 4B, the degrader 30 is configured to be closer to the upstream side in the scanning direction of the charged particle beam R, outward in the scanning direction. "Outward in the scanning direction" means "toward a direction away from the base axis AX in a direction perpendicular to the base axis AX of the charged particle beam R". In addition, the degrader 30 has an upstream side surface 30a located on an upstream side in the scanning direction of the charged particle beam R and a downstream side surface 30b located on a downstream side in the scanning direction of the charged particle beam R. Each of the upstream side surface 30a and the downstream side surface 30b are configured to be closer to the upstream side in the scanning direction of the charged particle beam R, outward in the scanning direction.

That is, assuming that a position where a charged particle beam R1 whose irradiation axis matches the base axis AX is incident on the upstream side surface 30a is an incidence position IP1 and a position where a charged particle beam R2 whose irradiation axis is deflected with respect to the base axis AX is incident on the upstream side surface 30a is an incidence position IP2, the incidence position IP2 outside the base axis AX is located on the more upstream side than the incidence position IP1. In addition, as the deflection angle of the charged particle beam R2 increases and accordingly the incidence position IP2 becomes away from the base axis AX and moves outward in the scanning direction, the incidence position IP2 is located on the upstream side. Assuming that a position where the charged particle beam R1 whose irradiation axis matches the base axis AX is emitted from the downstream side surface 30b is an emission position EP1 and a position where the charged particle beam R2 whose irradiation axis is deflected with respect to the base axis AX is emitted from the downstream side surface 30b is an emission position EP2, the emission position EP2 outside the base axis AX is located on the more upstream side than the emission position EP1. In addition, as the deflection angle of the charged particle beam R2 increases and accordingly the emission position EP2 becomes away from the base axis AX and moves outward in the scanning direction, the emission position EP2 becomes located on the upstream side.

The degrader 30 is configured to be closer to the upstream side in the scanning direction of the charged particle beam R outward in the X direction as shown in FIG. 4A and closer to the upstream side in the scanning direction of the charged particle beam R outward in the Y direction as shown in FIG. 4B. As a whole, the degrader 30 is formed in a bowl shape such that a portion on the base axis AX side becomes convex toward the downstream side. Accordingly, the upstream side surface 30a becomes a concave lens shaped surface, and the downstream side surface 30b becomes a convex lens shaped surface. In addition, the shape of the degrader 30 when viewed from the Z direction is not particularly limited, and may be a circle, a square, or a polygon.

Specifically, the degrader 30 is curved so as to be closer to the upstream side in the scanning direction of the charged particle beam R outward in the X direction as shown in FIG. 4A, and is curved so as to be closer to the upstream side in the scanning direction of the charged particle beam R outward in the Y direction as shown in FIG. 4B. The upstream side surface 30a becomes a concave lens shaped curved surface, and the downstream side surface 30b becomes a convex lens shaped curved surface.

As shown in FIG. 4A, for the curvature in the X direction, the upstream side surface 30a and the downstream side surface 30b may be curved with a predetermined radius of curvature (preferably, the radius of curvature of the downstream side surface 30b is a value obtained by adding the thickness A of the degrader 30 to the radius of curvature of the upstream side surface 30a) with the reference point SP of deflection by the X-direction scanning electromagnet 3a as the center of curvature. In this case, the passing distance of the charged particle beam R2, of which the irradiation axis has been deflected with respect to the base axis AX, within the degrader 30 can be made to be constant or approximately constant regardless of the deflection angle θ. In addition, the reference point SP is an intersection between the base axis AX and the irradiation axis of the deflected charged particle beam R2, and is set at the approximately central position of the X-direction scanning electromagnet 3a in the Z direction. However, the center of curvature does not necessarily need to be set to the reference point SP, and may be set at any position on the base axis AX as long as it is near the X-direction scanning electromagnet 3a.

As shown in FIG. 4B, for the curvature in the Y direction, the upstream side surface 30a and the downstream side surface 30b may be curved with a predetermined radius of curvature (preferably, the radius of curvature of the downstream side surface 30b is a value obtained by adding the thickness A of the degrader 30 to the radius of curvature of the upstream side surface 30a) with the reference point SP of deflection by the Y-direction scanning electromagnet 3b as the center of curvature. In this case, the passing distance of the charged particle beam R2, of which the irradiation axis has been deflected with respect to the base axis AX, within the degrader 30 can be made to be constant or approximately constant regardless of the deflection angle θ. In addition, the reference point SP is an intersection between the base axis AX and the irradiation axis of the deflected charged particle beam R2, and is set at the approximately central position of the Y-direction scanning electromagnet 3b in the Z direction. However, the center of curvature does not necessarily need to be set to the reference point SP, and may be set at any position on the base axis AX as long as it is near the Y-direction scanning electromagnet 3b.

When the center of curvature with respect to the curvature in the X direction and the center of curvature with respect to the curvature in the Y direction are set at different positions, the curvature of the upstream side surface 30a and the downstream side surface 30b is set by superimposing the curvature component in the X direction and the curvature component in the Y direction. Alternatively, the center of curvature with respect to the curvature in the X direction and the center of curvature with respect to the curvature in the Y direction may be made to match each other. In this case, the radius of curvature of the upstream side surface 30a and the downstream side surface 30b can be made to be constant regardless of positions in the X and Y directions. In addition, the radius of curvature of the upstream side surface 30a can be set to 1500 mm to 3000 mm in the case of the scanning method and to 1500 mm to 3000 mm in the case of the wobbler method.

In addition, the method of setting the curvature of the upstream side surface 30a and the downstream side surface 30b using the center of curvature and the radius of curvature as described above is just an example, and the upstream side surface 30a and the downstream side surface 30b can be curved in any method as long as the passing distance of the charged particle beam R within the degrader 30 can be constant or approximately constant.

In addition, although the example in which the upstream side surface 30a and the downstream side surface 30b are curved in both the X and Y directions has been described in FIGS. 4A and 4B, the upstream side surface 30a and the downstream side surface 30b may be curved only in one direction in the scanning direction, or may be curved either in the X direction or in the Y direction.

Figure 6:
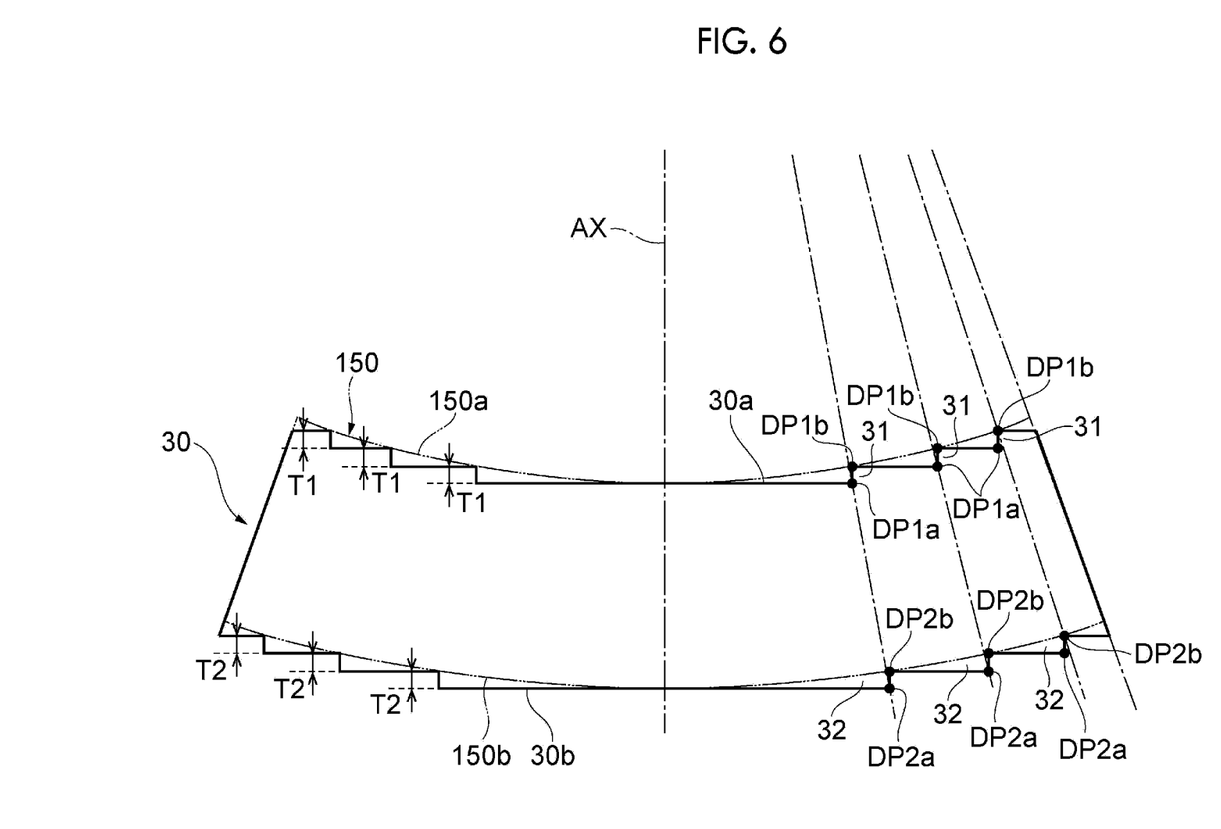
FIG. 6 is a schematic diagram showing the configuration of a degrader in a modification.

In addition, curved surfaces of the upstream side surface 30a and the downstream side surface 30b may be approximately reproduced instead of making the upstream side surface 30a and the downstream side surface 30b curved by curving the degrader 30. For example, as shown in FIG. 6, the curved surfaces can be approximately formed by forming a plurality of stepped portions 31 and 32 on the upstream side surface 30a and the downstream side surface 30b. In addition, FIG. 6 schematically shows the curvature emphasized in order to describe the method of setting the stepped portions 31 and 32. In this configuration, the degrader 30 has the stepped portions 31 and 32 that are located on the upstream side in the scanning direction of the charged particle beam R stepwise, outward in the scanning direction. The upstream side surface 30a has the stepped portion 31 located on the upstream side in the scanning direction of the charged particle beam R stepwise, outward in the scanning direction, and the downstream side surface 30b has the stepped portion 32 located on the upstream side in the scanning direction of the charged particle beam R stepwise, outward in the scanning direction.

Specifically, on the upstream side surface 30a, a plane perpendicular to the base axis AX extends from the base axis AX to the first stepped portion 31, outward in the scanning direction, rising (which may be vertical rising or may not be vertical rising) toward the upstream side in the scanning direction of the charged particle beam R occurs by a predetermined height at the position of the first stepped portion 31, and another plane perpendicular to the base axis AX extends to the next stepped portion 31. By repeating the above, a plurality of planes (planes perpendicular to the base axis AX) are formed on the upstream side surface 30a so as to be closer to the upstream side in the scanning direction of the charged particle beam R, outward in the scanning direction. On the downstream side surface 30b, a plane perpendicular to the base axis AX extends from the base axis AX to the first stepped portion 32, outward in the scanning direction, falling (which may be vertical falling or may not be vertical falling) toward the upstream side in the scanning direction of the charged particle beam R occurs by a predetermined height at the position of the first stepped portion 32, and a plane perpendicular to the base axis AX extends to the next stepped portion 32. By repeating the above, a plurality of planes (planes perpendicular to the base axis AX) are formed on the downstream side surface 30b so as to be closer to the upstream side in the scanning direction of the charged particle beam R, outward in the scanning direction.

A method of setting the stepped portions 31 and 32 of the stepwise degrader 30 (here, referred to as a stepped degrader 30) will be described with reference to FIG. 6. In addition, a degrader 150 that is curved (here, referred to as a curved degrader 150) is shown by the two-dot chain line. It is assumed that the stepped degrader 30 is set on the basis of the curved degrader 150. First, on the basis of an upstream side surface 150a of the curved degrader 150, the stepped portion 31 of the upstream side surface 30a of the stepped degrader 30 is set. However, the method of setting the stepped portions 31 and 32 shown below is just an example, and may be set in any method.

The stepped portion 31 has a step difference point DP1a on the downstream side and a step difference point DP1b on the upstream side, and is set such that the step difference point DP1b on the upstream side matches the upstream side surface 150a of the curved degrader 150. The step difference point DP1a on the downstream side of one stepped portion 31 is set such that the position of the step difference point DP1a in the Z direction is the same as the step difference point DP1b on the upstream side of the stepped portion 31 adjacent to the inside of the scanning direction. Under these conditions, the step difference points DP1a and DP2b are set such that the height T1 of the step difference in each stepped portion 31 is almost the same. For example, when the distance to the center of curvature of the curved degrader 150 is 2 m, the height T1 of the stepped portion 31 is 0.7 mm in the case of a 4-stage configuration (configuration in which a plane perpendicular to the base axis AX is formed in four stages). In practice, from the point of view of machining accuracy, it is preferable to adopt a configuration of nine stages or so in which the height T1 is 0.3 mm.

Then, on the basis of a downstream side surface 150b of the curved degrader 150, the stepped portion 31 of the downstream side surface 30b of the stepped degrader 30 is set. The stepped portion 32 has a step difference point DP2a on the downstream side and a step difference point DP2b on the upstream side, and is set such that the step difference point DP2b on the upstream side matches the upstream side surface 150a of the curved degrader 150. The step difference point DP2a on the downstream side of one stepped portion 32 is set such that the position of the step difference point DP2a in the Z direction is the same as the step difference point DP2b on the upstream side of the stepped portion 32 adjacent to the inside of the scanning direction. The step difference point DP2b of the downstream side surface 30b is set on the straight line connecting the center of curvature and the step difference point DP1b of the upstream side surface 30a. In addition, the step difference point DP2a of the downstream side surface 30b is set on the straight line connecting the center of curvature and the step difference point DP1a of the upstream side surface 30a. In addition, the distance of the step difference points DP1a and DP1b of the upstream side surface 30a from the base axis AX is different from the distance of the step difference points DP2a and DP2b of the downstream side surface 30b from the base axis AX.

Next, the operation and effect of the degrader 30 according to the present embodiment will be described.

First, a degrader in the related art will be described with reference to FIG. 5 for comparison. A degrader 130 in the related art has a plate shape (with a fixed thickness of A) extending in the X and Y directions, and an upstream side surface 130a and a downstream side surface 130b of the degrader 30 are planes perpendicular to the base axis AX. That is, cross-sections of the upstream side surface 130a and the downstream side surface 130b in the irradiation direction are rectangles. When the degrader 130 is used, the charged particle beam R1 whose irradiation axis matches the base axis AX is perpendicularly incident on the upstream side surface 130a of the degrader 130. Accordingly, the passing distance within the degrader 130 is A which is the same as the thickness of the degrader 130. On the other hand, the passing distance of the charged particle beam R2, of which the irradiation axis is deflected with respect to the base axis AX, within the degrader 30 is larger than A. Specifically, when the irradiation axis of the charged particle beam R2 is deflected at the deflection angle θ with respect to the base axis AX, the passing distance within the degrader 130 is "A/cos θ". Accordingly, the range of the charged particle beam R2 is shorter than that of the charged particle beam R1.

Figure 7:
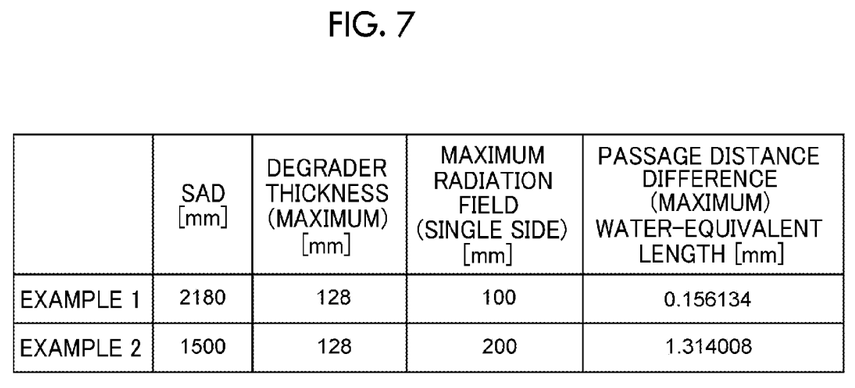
FIG. 7 is a table showing the relationship between each condition of the charged particle beam irradiation apparatus and the passing distance of a charged particle beam within the degrader.

Therefore, when creating a scanning pattern of the charged particle beam R for a predetermined layer LT without taking into consideration the above-described relationship between the passing distance within the degrader 130 and the range and the charged particle beam irradiation apparatus 1 irradiates the charged particle beam R on the basis of the scanning pattern, the charged particle beam R1 whose irradiation axis matches the base axis AX is irradiated to the layer LT as planned, but the charged particle beam R2 whose irradiation axis is deflected with respect to the base axis AX is irradiated to a position on the upstream side of the layer LT. For this reason, since an actual dose of the charged particle beam R irradiated to a predetermined position of the tumor 14 is different from that planned in the treatment planning, there is a problem in that the irradiation accuracy of the charged particle beam is reduced. In addition, although the case of the scanning method is described as an example in FIG. 5, the same problem also arises in the case of the wobbler method. For example, as shown in FIG. 7, when a source-axis distance (SAD: a distance between the beam source and the rotation axis) is shortened by miniaturization of the gantry or when the tumor 14 is large and the radiation field is increased, a difference in the passing distance of the charged particle beam R within the degrader 130 is increased.

On the other hand, in the charged particle beam irradiation apparatus 1 according to the present embodiment, the degrader 30 is configured to be closer to the upstream side in the scanning direction of the charged particle beam R, outward in the scanning direction. Then, the overall shape of the degrader 30 in the scanning direction becomes a shape curved with respect to the scanning electromagnets 3a and 3b that are the origins of deflection of the charged particle beam R (the degrader 30 has a curved shape in the case of FIGS. 4A and 4B, and the degrader 30 has an approximately curved shape when the stepped portions 31 and 32 are formed as shown in FIG. 6). Therefore, it is possible to suppress an increase in the passing distance of the charged particle beam R, which has a large deflection angle θ, within the degrader 30. For example, as shown in FIG. 4A, when the degrader 30 has a curved shape with the fixed thickness A, the passing distance of the charged particle beam R1 whose irradiation axis matches the base axis AX within the degrader 30 is equal to the thickness A, and the passing distance of the charged particle beam R2 whose irradiation axis is deflected with respect to the base axis AX within the degrader 30 is also equal (or approximately equally) to the thickness A. Accordingly, since it is possible to reduce a difference between the passing distance of the charged particle beam R having a small deflection angle θ within the degrader 30 and the passing distance of the charged particle beam R having a large deflection angle θ within the degrader 30, it is possible to suppress a change in the range of the charged particle beam R due to the deflection angle θ. In this manner, it is possible to irradiate a charged particle beam with high accuracy.

In addition, in the charged particle beam irradiation apparatus 1, the upstream side surface 30a of the degrader 30 is configured to be closer to the upstream side in the scanning direction of the charged particle beam R, outward in the scanning direction, and the downstream side surface 30b is configured to be closer to the upstream side in the scanning direction of the charged particle beam R, outward in the scanning direction. With this configuration, the overall shape of the degrader 30 in the scanning direction can be made to be a curved shape in a state where the thickness of the degrader 30 is constant or approximately constant. Accordingly, the passing distance of the charged particle beam R within the degrader 30 according to the deflection angle θ can be made to be constant or approximately constant.

In addition, in the charged particle beam irradiation apparatus 1, the degrader 30 may have the stepped portions 31 and 32 that are located on the upstream side in the scanning direction of the charged particle beam R stepwise, outward in the scanning direction. The shape of the degrader 30 can be made to be an approximately curved shape in the scanning direction by forming the plurality of stepped portions 31 and 32. As a result, machining of the degrader for forming a shape, in which the change in the range of the charged particle beam R according to the deflection angle θ can be suppressed, can be easily performed (compared with machining for forming the degrader 30 in a curved shape as shown in FIGS. 4A and 4B).

In addition, in the charged particle beam irradiation apparatus 1, the degrader 30 may be curved so as to be closer to the upstream side in the scanning direction of the charged particle beam R, outward in the scanning direction. For example, when the stepped portions 31 and 32 are provided as shown in FIG. 6, a slight variation in the passing distance of the charged particle beam R within the degrader 30 is caused by the deflection angle θ. However, since the degrader 30 is curved as shown in FIGS. 4A and 4B, the passing distance of the charged particle beam R within the degrader 30 according to the deflection angle θ can be made to be exactly constant or approximately constant in the entire region in the scanning direction. As a result, it is possible to further improve the accuracy of irradiation of the charged particle beam R.

In addition, in the charged particle beam irradiation apparatus 1, the degrader 30 is configured to be closer to the upstream side in the scanning direction of the charged particle beam R outward in the X direction and closer to the upstream side in the scanning direction of the charged particle beam R outward in the Y direction. Accordingly, at any position in both the X and Y directions, the passing distance of the charged particle beam R within the degrader 30 according to the deflection angle θ can be made to be constant or approximately constant. As a result, it is possible to further improve the accuracy of irradiation of the charged particle beam R.

The present invention is not limited to the above-described embodiment.

For example, although the example in which the plate-like degrader 30 is used has been described in the embodiment described above, it is also possible to use degraders 40 and 50 shown in FIGS. 8A, 8B, 9A, and 9B.

Figure 8A:
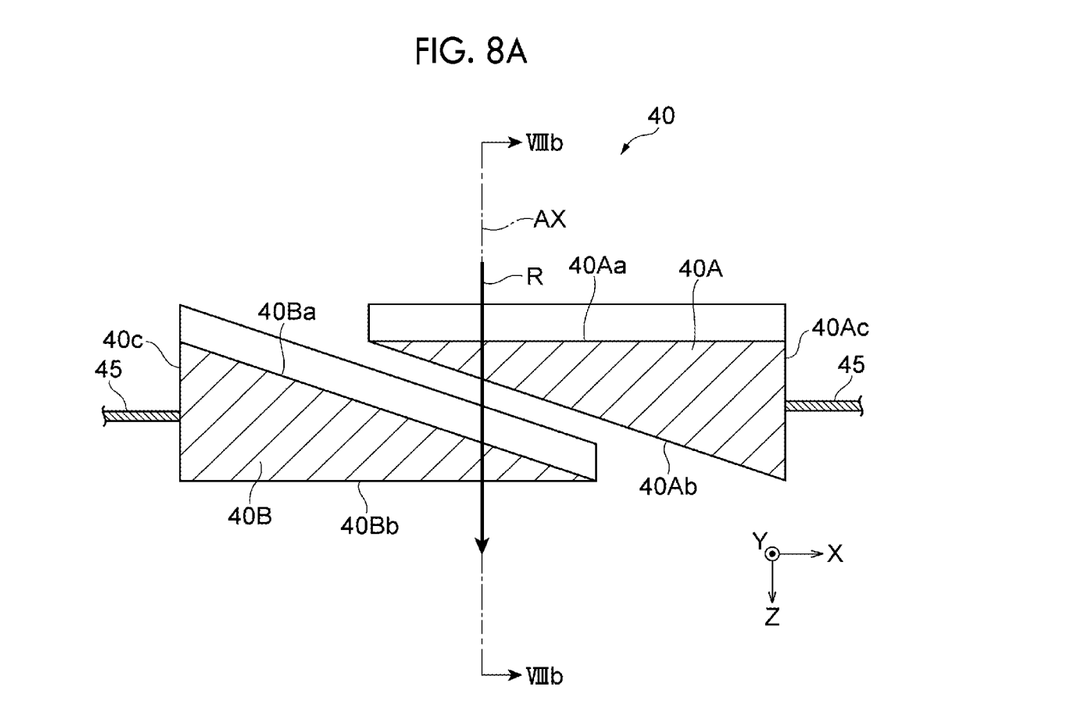
FIGS. 8A and 8B are schematic diagrams showing a degrader in a modification.
Figure 8B:
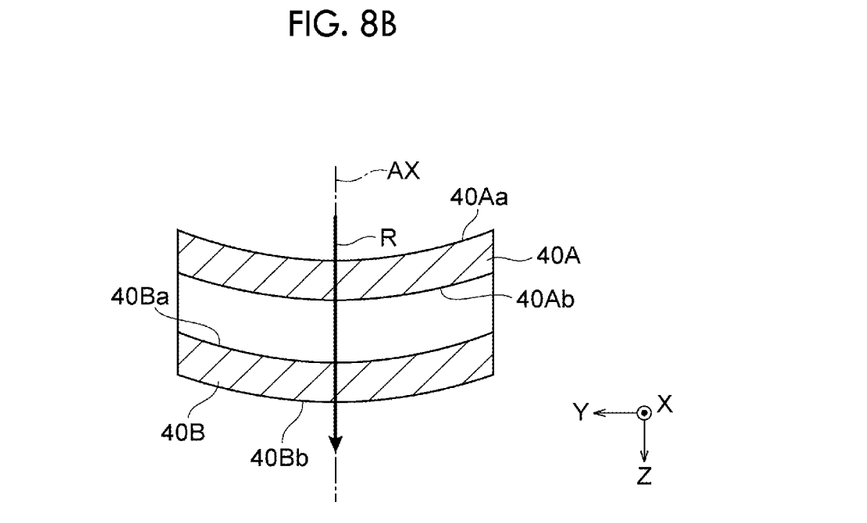

As shown in FIGS. 8A and 8B, certain embodiments of the present invention may be applied to the wedge-shaped degrader 40. In the degrader 40 shown in FIG. 8A, degraders 40A and 40B having right-angled triangular cross-sections are made to face each other in the Z direction, and each of the degraders 40A and 40B are moved in the X direction by an actuator 45 in order to adjust the range. In addition, FIG. 8A shows cross-sections when the degraders 40A and 40B are cut by the XZ plane at the position of the base axis AX, so that the configuration can be easily understood. FIG. 8B also shows the cross-section of a portion (portion on the right side from the base axis AX in the plane of the drawing) cut in FIG. 8A.

As shown in FIG. 8A, the degrader 40A disposed on the upstream side has an upstream side surface 40Aa corresponding to the long side (perpendicular to the base axis AX) of the cross-section of the right-angled triangle, a downstream side surface 40Ab corresponding to the hypotenuse, and a side surface 40Ac corresponding to the short side (parallel to the base axis AX). The actuator 45 for making the degrader 40A reciprocate in the X direction is connected to the side surface 40Ac. The degrader 40B disposed on the downstream side has an upstream side surface 40Ba corresponding to the hypotenuse of the cross-section of the right-angled triangle, a downstream side surface 40Bb corresponding to the long side (perpendicular to the base axis AX), and a side surface 40Bc corresponding to the short side (parallel to the base axis AX). The actuator 45 for making the degrader 40B reciprocate in the X direction is connected to the side surface 40Bc. The downstream side surface 40Ab of the degrader 40A and the upstream side surface 40Ba of the degrader 40B face each other so as to be parallel to each other. By moving the degraders 40A and 40B in the X direction using the actuator 45, it is possible to adjust the passing distance of the charged particle beam R passing through the inside of the degraders 40A and 40B (sum of the passing distance of the charged particle beam R passing through the inside of the degrader 40A and the passing distance of the charged particle beam R passing through the inside of the degrader 40B).

In addition, in the degrader 40B, only the upstream side surface 40Ba is configured to be closer to the upstream side in the scanning direction outward in the X direction, but the downstream side surface 40Bb is not configured to be closer to the upstream side in the scanning direction outward in the X direction. Accordingly, the degrader 40B is configured such that the thickness of the degrader 40B increases outward in the X direction. It is assumed that such a shape does not correspond to the shape in which "the degrader is configured to be closer to the upstream side in the scanning direction of the charged particle beam, outward in the scanning direction" in the present invention.

As shown in FIG. 8B, each of degraders 40A and 40B is configured to be closer to the upstream side in the scanning direction of the charged particle beam R, outward in the scanning direction (here, Y direction). The upstream side surface 40Aa and the downstream side surface 40Ab of the degrader 40A are curved with respect to the Y direction, and are configured to be closer to the upstream side in the scanning direction of the charged particle beam R outward in the Y direction. The upstream side surface 40Ba and the downstream side surface 40Bb of the degrader 40B are curved with respect to the Y direction, and are configured to be closer to the upstream side in the scanning direction of the charged particle beam R outward in the Y direction. Accordingly, the passing distance of the charged particle beam R, which is scanned in the Y direction, within the degraders 40A and 40B can be made to be constant or approximately constant. In addition, it is also possible to form the upstream side surfaces 40Aa and 40Ba and the downstream side surfaces 40Ab and 40Bb as stepwise surfaces as shown in FIG. 6 instead of curved surfaces.

Figure 9A:
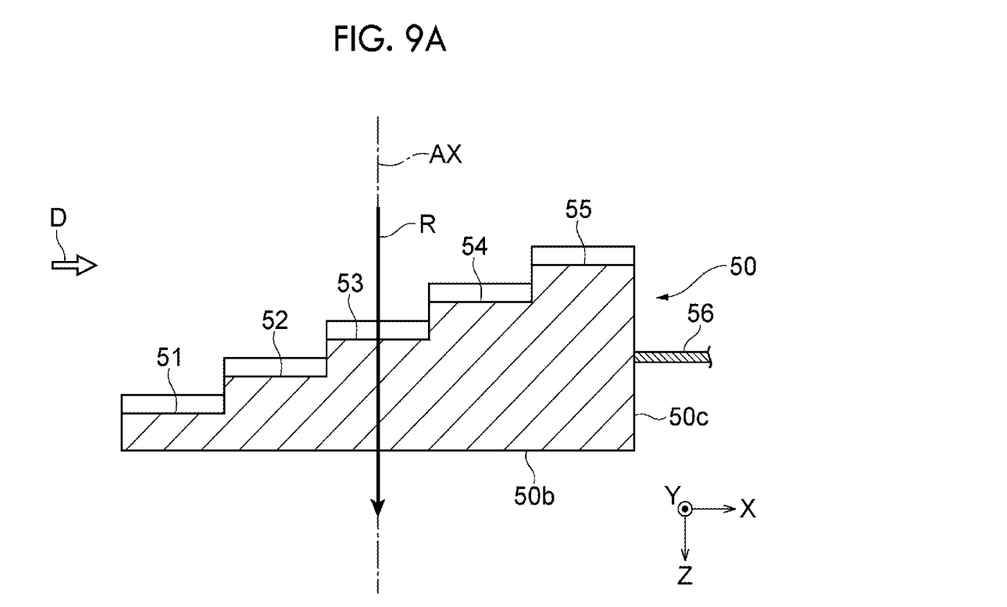
FIGS. 9A and 9B are schematic diagrams showing a degrader in a modification.
Figure 9B:
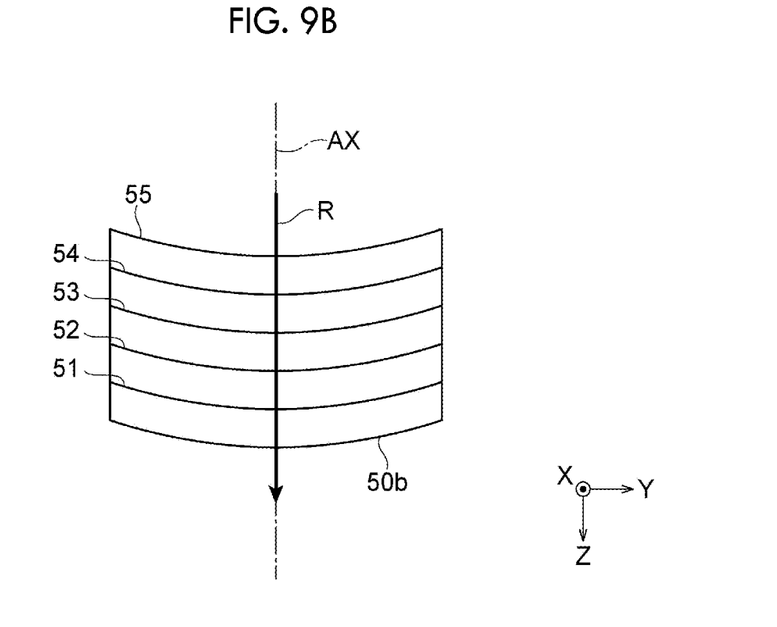

As shown in FIGS. 9A and 9B, certain embodiments of the present invention maybe applied to a stepwise degrader 50. The degrader 50 shown in FIG. 9A is formed in a stepped shape to have a plurality of portions with different thicknesses, and adjusts the range by changing the thickness of a portion on which the charged particle beam R is incident. In addition, FIG. 9A shows a cross-section when the degrader 50 is cut by the XZ plane at the position of the base axis AX, so that the configuration can be easily understood. FIG. 9B is a diagram viewed from the direction of the arrow D in FIG. 9A. FIG. 9B also shows the cross-section of a portion (portion on the right side from the base axis AX in the plane of the drawing) cut in FIG. 9A.

As shown in FIG. 9A, the degrader 50 has a configuration in which the thickness changes stepwise along the X direction. That is, the position of a downstream side surface 50b of the degrader 50 in the Z direction is constant in the entire region in the X direction, while upstream side surfaces 51, 52, 53, 54, and 55 are disposed in this order on the upstream side in the Z direction. When the degrader 50 is used, the range is adjusted by changing the upstream side surface on which the charged particle beam R is incident. An actuator 56 for making the degrader 50 reciprocate in the X direction is connected to the side surface 50c of the degrader 50.

As shown in FIG. 9B, the degrader 50 is configured to be closer to the upstream side in the scanning direction of the charged particle beam R, outward in the scanning direction (here, Y direction). The upstream side surfaces 51 to 55 and the downstream side surface 50b of the degrader 50 are curved with respect to the Y direction, and are configured to be closer to the upstream side in the scanning direction of the charged particle beam R outward in the Y direction. Accordingly, the passing distance of the charged particle beam R, which is scanned in the Y direction, within the degrader 50 can be made to be constant or approximately constant. In addition, it is also possible to form the upstream side surfaces 51 to 55 and the downstream side surface 50b as stepwise surfaces as shown in FIG. 6 instead of curved surfaces.

In addition, in the degrader 50, only the upstream side surfaces have portions (portions on the right side from the base axis AX in the plane of FIG. 9A) located on the upstream side in the scanning direction stepwise toward one direction of the outside in the X direction, but the downstream side surface 50b is not configured to be closer to the upstream side in the scanning direction outward in the X direction. Accordingly, the degrader 50 is configured such that the thickness of the degrader 50 increases toward one direction of the outside in the X direction. It is assumed that such a shape does not correspond to the shape in which "the degrader is configured to be closer to the upstream side in the scanning direction of the charged particle beam, outward in the scanning direction" in the present invention.

It should be understood that the invention is not limited to the above-described embodiment, but may be modified into various forms on the basis of the spirit of the invention. Additionally, the modifications are included in the scope of the invention.

What is claimed is:

1. A charged particle beam irradiation apparatus comprising:
   a scanning electromagnet that scans a charged particle beam according to a predetermined scan pattern; and
   a segmental arch shaped degrader that is provided on a downstream side of the scanning electromagnet extending in a scanning direction of the charged particle beam and adjusts a range of the charged particle beam by reducing energy of the charged particle beam,
   wherein the degrader is not configured to shape a three-dimensional shape of a portion of a maximum arrival depth of the charged particle beam according to a shape of a tumor portion at a maximum depth.

2. The charged particle beam irradiation apparatus according to claim 1,
   wherein the degrader comprises a concave upstream side surface located on the upstream side in the scanning direction of the charged particle beam and a convex downstream side surface located on a downstream side in the scanning direction of the charged particle beam.

3. The charged particle beam irradiation apparatus according to claim 2,
   wherein the degrader has a plurality of stepped portions that are located on the upstream side in the scanning direction of the charged particle beam stepwise, outward in the scanning direction.

4. The charged particle beam irradiation apparatus according to claim 2,
   wherein the degrader is curved so as to be closer to the upstream side in the scanning direction of the charged particle beam, outward in the scanning direction.

5. The charged particle beam irradiation apparatus according to claim 1,
   wherein the scanning direction includes a first scanning direction and a second scanning direction, the second scanning direction being perpendicular to the first scanning direction, and
   the degrader is configured to be closer to the upstream side in the first scanning direction of the charged particle beam outward in the first scanning direction and closer to the upstream side in the second scanning direction of the charged particle beam outward in the second scanning direction.

6. The charged particle beam irradiation apparatus according to claim 1, further comprising a convergence body that converges the charged particle beam.

7. The charged particle beam irradiation apparatus according to claim 6, further comprising an irradiation nozzle that houses the scanning electromagnet, the degrader and the convergence body and irradiates the charged particle beam.

8. A charged particle beam irradiation apparatus comprising:
   a scanning electromagnet that scans a charged particle beam;
   a segmental arch shaped degrader that is provided on a downstream side of the scanning electromagnet in a scanning direction of the charged particle beam and adjusts a range of the charged particle beam by reducing energy of the charged particle beam;
   a scatterer that diffuses the charged particle beam that pass through the scatterer; and
   a bolus that shapes a three-dimensional shape of a portion of a maximum arrival depth of the charged particle beam according to a shape of a tumor portion at a maximum depth;
   wherein the degrader is configured to be closer to an upstream side in the scanning direction of the charged particle beam, outward in the scanning direction.

9. The charged particle beam irradiation apparatus according to claim 8,
   wherein the degrader comprises a concave upstream side surface located on the upstream side in the scanning direction of the charged particle beam and a convex downstream side surface located on a downstream side in the scanning direction of the charged particle beam.

10. The charged particle beam irradiation apparatus according to claim 9,
    wherein the degrader has a plurality of stepped portions that are located on the upstream side in the scanning direction of the charged particle beam stepwise, outward in the scanning direction.

* * * * *